United States Patent
Takahashi et al.

(10) Patent No.: US 10,434,335 B2
(45) Date of Patent: Oct. 8, 2019

(54) POSITIONING APPARATUS AND METHOD OF POSITIONING BY GENERATION OF DRR IMAGE FROM X-RAY CT IMAGE DATA

(71) Applicant: SHIMADZU CORPORATION, Kyoto (JP)

(72) Inventors: Wataru Takahashi, Kyoto (JP); Shinichiro Mori, Chiba (JP)

(73) Assignee: SHIMADZU CORPORATION, Kyoto (JP)

( * ) Notice: Subject to any disclaimer, the term of this patent is extended or adjusted under 35 U.S.C. 154(b) by 223 days.

(21) Appl. No.: 15/473,708

(22) Filed: Mar. 30, 2017

(65) Prior Publication Data

US 2018/0280727 A1    Oct. 4, 2018

(51) Int. Cl.
*A61N 5/10*     (2006.01)
*A61B 6/03*     (2006.01)
(Continued)

(52) U.S. Cl.
CPC ............ *A61N 5/1049* (2013.01); *A61B 6/032* (2013.01); *A61B 6/035* (2013.01); *A61B 6/04* (2013.01); *A61B 6/52* (2013.01); *A61B 6/5205* (2013.01); *A61B 6/5211* (2013.01); *G06T 7/0012* (2013.01); *G06T 7/73* (2017.01); *G06T 11/005* (2013.01); *A61N 2005/1061* (2013.01);
(Continued)

(58) Field of Classification Search
CPC ..... A61B 6/052; A61B 6/5205; A61B 6/5211; A61B 6/04; A61B 6/035; A61B 6/52; A61N 5/1049; A61N 2005/1061; A61N 2005/1062

USPC ............................ 378/4, 62, 65, 20, 68, 205
See application file for complete search history.

(56) References Cited

U.S. PATENT DOCUMENTS 5,740,225 A * 4/1998 Nabatame .............. A61N 5/103
                                                                    378/65
5,901,199 A * 5/1999 Murphy .................... A61B 6/08
                                                                    378/65
(Continued)

FOREIGN PATENT DOCUMENTS

JP     2007-282877     4/2006
JP     A2009-189461     2/2008
(Continued)

OTHER PUBLICATIONS

JP2014-190101, Notification of Reason for Refusal, dated Feb. 2, 2018, 4 pages—English, 4 pages—Japanese.

*Primary Examiner* — Allen C. Ho
(74) *Attorney, Agent, or Firm* — Andrew F. Young, Esq.; Lackenbach Siegel, LLP

(57) ABSTRACT

A positioning apparatus automatically performs a patient positioning calculation at high speed and a positioning method. A positioning apparatus 40 has, as functional components, a DRR image generation element 41 that generates the DRR image based on the CT image data, an optimization element 43 that calculates the positional gap of the patient 57 by optimizing the fluoroscopic projection parameters; and an initial parameter adjustment element 42 that changes the initial position of the fluoroscopic projection parameters prior to optimization of fluoroscopic projection parameters with regard to the rotatable and translation of the CT image data relative to the optimization element 43.

6 Claims, 14 Drawing Sheets

(51) Int. Cl.
*G06T 7/00* (2017.01)
*A61B 6/00* (2006.01)
*A61B 6/04* (2006.01)
*G06T 7/73* (2017.01)
*G06T 11/00* (2006.01)

(52) U.S. Cl.
CPC ........... *A61N 2005/1062* (2013.01); *G06T 2207/10121* (2013.01); *G06T 2207/10124* (2013.01); *G06T 2207/20068* (2013.01)

(56) References Cited

U.S. PATENT DOCUMENTS

| | | | | |
|---|---|---|---|---|
| 6,516,046 B1* | 2/2003 | Fröhlich | ............... | A61B 6/04 378/205 |
| 6,674,833 B2* | 1/2004 | Shahidi | ............... | A61B 90/36 378/4 |
| 6,714,810 B2* | 3/2004 | Grzeszczuk | ............... | A61B 90/36 600/427 |
| 6,865,253 B2* | 3/2005 | Blumhofer | ............... | A61B 6/547 378/205 |
| 6,907,281 B2* | 6/2005 | Grzeszczuk | ............... | A61B 90/36 378/41 |
| 7,010,080 B2* | 3/2006 | Mitschke | ............... | A61B 6/12 378/15 |
| 7,072,435 B2* | 7/2006 | Metz | ............... | A61B 6/032 378/62 |
| 7,187,792 B2* | 3/2007 | Fu | ............... | A61N 5/1049 382/128 |
| 7,212,608 B2* | 5/2007 | Nagamine | ............... | A61B 6/04 378/205 |
| 7,231,076 B2* | 6/2007 | Fu | ............... | G06K 9/3233 378/4 |
| 7,260,426 B2* | 8/2007 | Schweikard | ............... | A61B 6/12 600/407 |
| 7,302,033 B2* | 11/2007 | Carrano | ............... | A61B 6/022 378/41 |
| 7,315,636 B2* | 1/2008 | Kuduvalli | ............... | G06T 11/008 128/922 |
| 7,349,522 B2* | 3/2008 | Yan | ............... | A61B 5/0816 378/65 |
| 7,366,278 B2* | 4/2008 | Fu | ............... | G06T 11/008 345/419 |
| 7,426,318 B2* | 9/2008 | Fu | ............... | G06T 7/344 382/294 |
| 7,436,928 B2* | 10/2008 | Urano | ............... | A61N 5/1049 378/64 |
| 7,453,983 B2* | 11/2008 | Schildkraut | ............... | A61N 5/1049 378/205 |
| 7,453,984 B2* | 11/2008 | Chen | ............... | A61N 5/1049 378/65 |
| 7,522,779 B2* | 4/2009 | Fu | ............... | A61B 6/5235 278/54 |
| 7,620,144 B2* | 11/2009 | Bodduluri | ............... | A61B 6/02 378/41 |
| 7,620,223 B2* | 11/2009 | Xu | ............... | A61B 6/032 382/128 |
| 7,623,623 B2* | 11/2009 | Raanes | ............... | A61N 5/1049 378/205 |
| 7,672,429 B2* | 3/2010 | Urano | ............... | A61N 5/1049 378/65 |
| 7,684,647 B2* | 3/2010 | Fu | ............... | G06K 9/32 345/630 |
| 7,689,019 B2* | 3/2010 | Boese | ............... | G03B 42/023 128/922 |
| 7,831,073 B2* | 11/2010 | Fu | ............... | A61N 5/1049 382/128 |
| 7,835,500 B2* | 11/2010 | Fu | ............... | A61B 6/4458 128/922 |
| 7,853,308 B2* | 12/2010 | Sauer | ............... | A61N 5/1049 378/62 |
| 7,894,649 B2* | 2/2011 | Fu | ............... | A61N 5/1049 382/128 |
| 8,073,230 B2* | 12/2011 | Fei | ............... | A61B 6/12 382/132 |
| 8,077,936 B2* | 12/2011 | Wang | ............... | G06Q 50/22 382/128 |
| 8,295,435 B2* | 10/2012 | Wang | ............... | A61N 5/10 378/65 |
| 8,315,356 B2* | 11/2012 | Core | ............... | A61N 5/1049 378/205 |
| 8,417,318 B2* | 4/2013 | West | ............... | A61B 6/12 600/424 |
| 8,457,372 B2* | 6/2013 | Fu | ............... | A61N 5/1049 382/128 |
| 8,471,222 B2* | 6/2013 | Handa | ............... | G06K 9/00 250/491.1 |
| 8,498,377 B2* | 7/2013 | Fadler | ............... | A61B 6/032 378/62 |
| 8,509,511 B2* | 8/2013 | Sakaguchi | ............... | A61B 6/12 382/131 |
| 8,824,630 B2* | 9/2014 | Maurer, Jr. | ............... | G06F 19/3481 378/20 |
| 8,831,706 B2* | 9/2014 | Fu | ............... | A61B 6/032 378/65 |
| 8,849,633 B2* | 9/2014 | Core | ............... | G16H 50/50 703/6 |
| 8,861,672 B2* | 10/2014 | Maltz | ............... | A61B 6/032 378/4 |
| 8,874,187 B2* | 10/2014 | Thomson | ............... | A61B 6/037 378/62 |
| 8,965,096 B2* | 2/2015 | Yamada | ............... | A61B 6/032 250/491.1 |
| 9,108,048 B2* | 8/2015 | Maurer, Jr. | ............... | A61B 6/5247 |
| 9,393,445 B2* | 7/2016 | Yamada | ............... | A61N 5/1039 |
| 9,886,760 B2* | 2/2018 | Liu | ............... | A61B 6/032 |
| 10,092,251 B2* | 10/2018 | Virshup | ............... | A61B 6/032 |

FOREIGN PATENT DOCUMENTS

| | | |
|---|---|---|
| JP | 2010-057810 | 9/2008 |
| JP | A2010-246733 | 4/2009 |
| JP | 2013-099431 | 11/2011 |

\* cited by examiner

POSITIONING APPARATUS AND METHOD OF POSITIONING BY GENERATION OF DRR IMAGE FROM X-RAY CT IMAGE DATA

CROSS REFERENCE TO RELATED APPLICATIONS

This application relates to, but does not claim priority from, JP 2014-190101 filed Sep. 18, 2014, the entire contents of which are incorporated herein by reference.

FIGURE SELECTED FOR PUBLICATION

FIG. 1

BACKGROUND OF THE INVENTION

Field of the Invention

The present invention relates to a positioning apparatus to position a patient when a radiation treatment is performed on the patient and a method of positioning therefor.

Description of the Related Art

The radiation relative to a radiation therapy, in which the radiation including an X-ray, an electron beam, a corpuscular radiation and so forth is irradiated to the affected area including a tumor of the patient and so forth, must be accurately irradiated to the affected area. When the radiation therapy is performed by using a radiation therapy apparatus, the radiation treatment planning is prepared prior to the radiotherapy treatment. And when the radiation therapy is actually performed, it is required to position the patient so as to follow the radiation treatment planning. Such positioning of the patient on a radiation therapy is conventionally performed by a medical engineer who operates the position of the radiotherapy table loading the patient while visually making sure the position indicated by a laser marker instrument. In addition, recently, it is proposed a method to position the patient by utilizing an X-ray fluoroscopic image (Patent Document 1-Patent Document 3).

Relative to such radiation therapy, the patient is restrained in the same posture on the radiotherapy table from the positioning to the end of the radiation treatment, so that such therapy can be stressful against the patient. A much quicker positioning for the patient is important to ease the stress of the patient. In addition, it is important to cut the occupied time of the radiation therapy apparatus per patient by highly accelerating the positioning so that much more patients can be given a therapeutic opportunity with the radiation therapy apparatus.

The positioning apparatus, according to the aspect of Patent Document 2, is proposed to cut the numbers of repetition of positioning by letting the device learn the position of rough positioning of the radiotherapy table based on the past radiotherapy table positioning data relative to the patient.

On the other hand, relative to positioning of a patient using utilizing X-ray radiographs, an geometric arrangement of the X-ray radiography system relative to the therapeutic device is reconstructed on the computer and a virtual fluoroscopic projection, i.e., DRR (Digital Reconstructed Radiography), that utilizes 3-dimensional image data collected by X-ray CT apparatus, when the radiation treatment planning is created, is executed. And a gap between the present position of the patient and the position set when the radiation treatment planning is created is calculated by estimating similarity between the actual X-ray radiograph and DRR image (image registration). The calculation cost for DRR is huge, so that Patent Document 3 discloses an automatic positioning apparatus by which the calculation cost needed to execute DRR can be cut, so that the position of the patient can be determined in a high speed on the radiation therapy.

RELATED PRIOR ART DOCUMENTS

Patent Document

Patent Document: Laid Open JP 2007-282877
Patent Document 2: JP Patent Published 2010-57810
Patent Document 3: JP Patent Published 2013-99431

ASPECTS AND SUMMARY OF THE INVENTION

Objects to be Solved by the Invention

Similarity between DRR image compared relative to the image registration and the actual image of the patient is generally subject to a non-convex function relative to the projection geometry when the DRR image is generated. Therefore, the solution obtained by optimization of the evaluation standard that evaluates the similarity between both images may be a local solution. On the other hand, it is effective that the default parameters, at the beginning of the optimization, set as close as possible to the optimized solution so that it can be prevented from getting such local solution when the optimization is calculated. Specifically, it is required that the radiographic geometry of the actual patient sets as close as possible to the DRR projection geometry at the step of roughly positioning prior to beginning the optimization operation.

Conventionally, a positioning of the patient prior to initiating the optimization operation, is manually executed by an operator, e.g., adjusting a laser marker instrument, or superimposing a DRR image displayed on the display and the actual fluoroscopic image of the patient via an input device, and so forth and a confirmation therefor is being run visually by the operator. Accordingly, the individual difference as to a determination due to the operator may affect the difference between accuracy levels relative to the positioning. In addition, it is undesirable that the accuracy level of the positioning to be accomplished, which must be in the relationship with the position of radiotherapy, varies depending on the skill level of the operator. In addition, according to the conventional method set forth above, the time needed for positioning has been tending to be longer.

In addition, according to the positioning apparatus according to Patent Document 2, the positioning is executed based on the past positioning data as to the radiation treatment table, so that when the first radiotherapy data relative to a divisional irradiation or a stereotactic radiosurgery irradiation, by which one radiation therapy can be completed, are performed, no past data can be generated and therefore, a conventional manual positioning should be carried out. In such cases, problems concerning to the individual operator discretion as to the positioning of the patient and that it takes a long time for positioning.

The purpose of the present invention is to solve the above objects and to provide a positioning apparatus that can perform automatically the positioning in a high speed and a positioning method using the same.

Means for Solving the Problem

According to the first invention, a positioning apparatus, for a patient, radiography device comprises: a DRR image generation element that obtains a DRR image by reconstructing a geometric arrangement of an X-ray radiography system on the computer and performing virtually a fluoroscopic projection on the X-ray CT image data collected in advance; and an optimization element that calculates the gap between a position of the patient when the X-ray CT image data are collected and an actual position of the patient at which the patient is fluoroscoped or imaged with an X-ray radiography system, wherein fluoroscopic projection parameters relative to rotation-and-translation of the X-ray CT image are optimized so that evaluation functions that evaluate the matching degree between the DRR image obtained by the DRR image generation element and the actual image obtained by fluoroscoping or radiographing the patient using the X-ray radiography system can be maximized; and further comprises; an initial parameter adjustment element that changes the initial position of the fluoroscopic projection parameters based on the rough positional gap; wherein the rough positional gap is calculated from the gap between the DRR image and the radiograph prior to beginning the optimization operation that optimizes the fluoroscopic projection parameters using the optimization element.

According to an aspect of the second invention, the initial parameter adjustment element respectively calculates 1-dimensional integral profile that integrates the DRR image in a predetermined direction and 1-dimensional integral profile that integrates the radiograph in a predetermined direction, and calculates the rough positional gap by executing the comparison between the 1-dimensional integral profiles of in the same direction as to the DRR image and the radiograph.

According to an aspect of the third invention, the initial parameter adjustment element calculates a similarity degree between histograms, as the 1-dimensional integral profile is a histogram, relative to comparison between 1-dimensional integral profiles in the same direction of the DRR image and the radiograph, and determines the initial position of the fluoroscopic projection parameters, at which the similarity degree between such histograms becomes maximum.

According to an aspect of the fourth invention, a method of positioning of a patient, comprises: a step of generating a DRR image obtained by reconstructing a geometric arrangement of an X-ray radiography system on a computer and performing virtually a fluoroscopic projection to an X-ray CT image data collected in advance; and a step of optimizing an calculation of a gap between a position of the patient when the X-ray CT image data are collected and an actual position of the patient at which the patient is fluoroscoped or imaged with the X-ray radiography system, wherein fluoroscopic projection parameters relative to rotation-and-parallel move of the X-ray CT image are optimized so that evaluation parameters that evaluate the matching degree between the DRR image obtained by the step of generating the DRR image and the actual image obtained by fluoroscoping or radiographing the patient using the X-ray radiography system can be maximized; and further comprises: a step of adjusting initial parameters that changes the initial position of the fluoroscopic projection parameters based on the rough positional gap; wherein the rough positional gap is calculated from the gap between the DRR image and the radiograph prior to beginning the optimization operation that optimizes the fluoroscopic projection parameters using the optimization step.

According to an aspect of the fifth invention, the step of adjusting the initial parameters respectively calculates 1-dimensional integral profile that integrates the DRR image in a predetermined direction and 1-dimensional integral profile that integrates the radiograph in a predetermined direction, and calculates the rough positional gap by executing the comparison between the 1-dimensional integral profiles of in the same direction relative to the DRR image and the radiograph.

According to an aspect of the sixth invention, the step of adjusting the initial parameters calculates a similarity degree between histograms, as the 1-dimensional integral profile is a histogram, relative to comparison between 1-dimensional integral profiles in the same direction of the DRR image and the radiograph, and determines the initial position of the fluoroscopic projection parameters, at which the similarity degree between such histograms becomes maximum.

Effect of the Invention

According to the aspect of the first invention and the fourth invention, an initial position of the initial fluoroscopic projection parameters can be automatically acquired using the DRR image and the radiograph taken prior to beginning the optimization operation by the optimization element. Accordingly, the workload on the operator for a conventional manual positioning can be reduced. In addition, the rough positional gap between the DRR image and the radiograph is calculated automatically, so that e.g., even when the first visit for the divisional radiation therapy is made, the radiotherapy throughput can be improved because such conventional manual step of adjusting the rough positioning could be skipped. Further, a manual operation for positioning by the operator is skippable, so that an accuracy level relative to the positioning of the patient can be performed with a high reproducibility regardless skills and experiences of the operator and in addition, the time needed to position the patient can be shortened. And the patient-time requirement for the radiation treatment can be cut, so that lessening the accuracy level of the positioning due to the move of the patient because of incapability of keeping the same posture (position) during positioning thereof can be suppressed and in addition, an arduous effort of the patient to keep the same posture (position) can be soothed.

According to the aspect of the second invention and the fifth invention, comparison between 1-dimensional integral profiles in the same direction of the DRR image and the radiograph is executed, so that a search for the position, at which similarity between images is highest, can be completed in a higher speed than executing the direct comparison between DRR image, which is a 2-dimensional image, and the radiograph. In addition, a mal-effect on the accuracy level of the positioning due to a noise component of each image can be reduced based on such integration.

According to aspects of the third invention and the sixth invention, a histogram intersection that calculates the similarity of between histograms, given the 1-dimensional integral profiles are histograms, is applied relative to the comparison between the DRR image and the radiograph, so that a strong and high speed search for the position, at which the similarity is highest, can be completed with regards to the difference of quality of images between the DRR image and the radiograph, the difference caused by radiography withor-without a radiotherapy table or a collimator, elements other than the patient, in each image, and the difference between concentrations.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
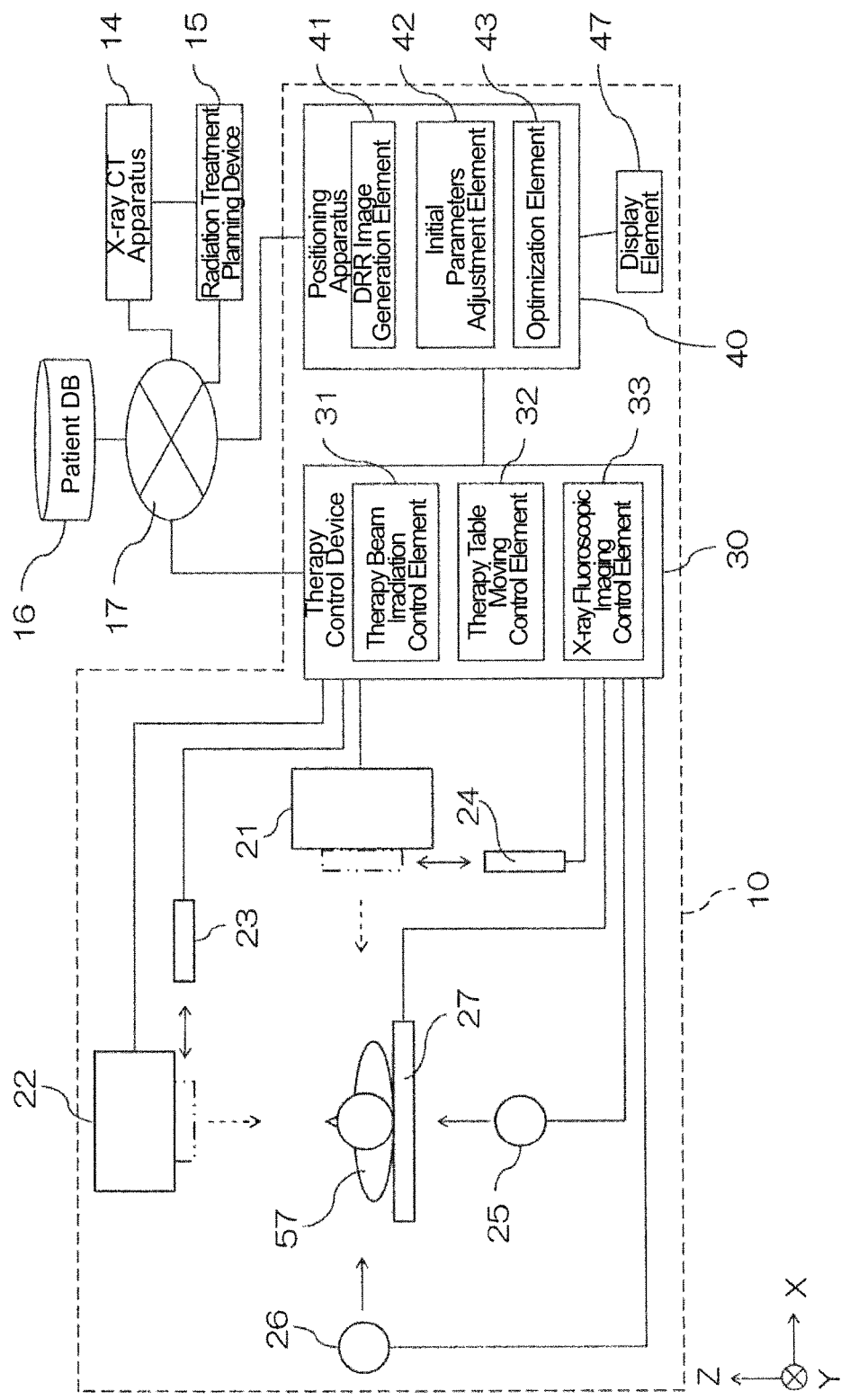
FIG. 1 is a schematic view illustrating a radiation therapy apparatus 10 comprising a positioning apparatus 40 according to the aspect of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The inventor sets forth Embodiments of the present invention based on the following FIGs. FIG. 1 is a schematic view illustrating a radiation therapy apparatus 10 comprising a positioning apparatus 40 according to the aspect of the present invention.

The radiation therapy apparatus 10 that performs a radiation therapy on the patient 57 lying on the radiotherapy table 27 comprises: a radiotherapy control device 30 that controls the operation of the entire radiotherapy apparatus and a positioning apparatus 40 according to the aspect of the present invention. The radiotherapy control device 30 and the positioning apparatus 40 are communicably connected each other. In addition, the radiotherapy control device 30 and the positioning apparatus 40 are connected to a patient DB (database) 16 that stores patient data, an X-ray CT apparatus 14 that obtains the 3-dimensional X-ray CT image data including the affected region of the patient 57 prior to the radiotherapy, and a radiation treatment planning device 15 that makes a radiation treatment planning based on the CT image data collected by the X-ray CT apparatus 14, via a network 17. In addition, the CT image data collected by the X-ray CT apparatus 14 and the radiation treatment planning of the patient 57 made by the radiation treatment planning device 15 are stored in the patient DB 16.

The radiotherapy control device 30 comprises: a CPU that executes the logic operation; a ROM that stores operation programs required to control the apparatus; and a RAM that stores temporally the data and so forth, when controlling; and controls the entire radiation therapy apparatus 10. In addition, the radiotherapy control device 30 comprises a radiotherapy beam irradiation control element 31, a radiotherapy table moving control device 32 and an X-ray fluoroscopic imaging control element 33 as a functional component.

The radiation therapy apparatus 10 comprises a horizontal irradiation port 21 and a vertical irradiation port 22 that irradiate a radiotherapy beam such as electron beam. Irradiation of the radiotherapy beam from the horizontal irradiation port 21 and the vertical irradiation port 22 is controlled by the radiotherapy irradiation control element 31. In addition, the radiotherapy table 27 of the radiation therapy apparatus 10 is movable and rotatable in 6 axes directions by the radiotherapy table moving control element 32.

The radiation therapy apparatus 10 comprises an X-ray radiography system capable of performing fluoroscopy-and-radiography in the two directions, including an X-ray detector 23 that detects X-rays irradiated from the X-ray tube 25, and then passed through the patient 57 and an X-ray detector 24 that detects X-rays irradiated from the X-ray tube 26 and then passed through the patient 57. An operation of an X-ray radiography system is controlled by the X-ray fluoroscopic imaging control element 33. Further, an image intensifier (I. I.) or a flat panel detector (FPD) is used as for the X-ray detector 23 and the X-ray detector 24.

The horizontal irradiation port 21 and the vertical irradiation port 22 relative to the radiation therapy apparatus 10 are fixed inside a room. And the X-ray detector 24 is movable between the radiography location (indicated by the phantom line (long-dashed and two short-dashed line referring to FIG. 1) in front of the horizontal irradiation port 21 facing the X-ray tube 26 sandwiching the patient 57 and the retracted (waiting) location (indicated by the solid line referring to FIG. 1) away from the horizontal irradiation port 21. Also, the X-ray detector 23 is movable between the radiography location (indicated by the phantom line (long-dashed and two short-dashed line referring to FIG. 1) in front of the horizontal irradiation port 22 facing the X-ray tube 25 sandwiching the patient 57 and the retracted (waiting) location (indicated by the solid line referring to FIG. 1) away from the horizontal irradiation port 22.

The positioning apparatus 40 is a computer comprising: a CPU that performs a logic operation; a ROM storing programs that perform the positioning for the patient 57; and a RAM that stores temporarily the calculation results and so forth and the display element 47 is connected thereto. The display element 47 is also operative as a Graphical User Interface (GUI) of the radiation therapy apparatus 10, and comprises e.g., a liquid crystal panel having a touchpanel function and so forth. The display element 47 displays the fluoroscopic image and the radiograph (hereafter collectively radiograph) based on the X-ray detected by the X-ray detector 23 and the X-ray detector 24, and 3-dimensional CT images collected by the X-ray CT apparatus 14 in advance. Further, the display 47 also displays the DRR image generated from the CT image data as set forth later and other information including irradiation data of the radiation and X-ray radiographic data and so forth.

The positioning apparatus 40 comprises, as functional components, a DRR image generation element 41 that generates the DRR image based on the CT image data; an optimization element 43 that calculates the positional gap of the patient 57 by optimizing the fluoroscopic projection parameters; and an initial parameter adjustment element 42 that changes the initial position of the fluoroscopic projection parameters when begins optimization prior to optimization of fluoroscopic projection parameters with regard to the rotation-and-translation of the CT image data relative to the optimization element 43.

The DRR image generation element 41 generates a DRR image by reading out CT image data collected by the X-ray CT apparatus in advance, reconstructing a geometric arrangement of an X-ray radiography system on the computer and performing also virtually a fluoroscopic projection on the CT image data. Specifically, the 2-dimensional image is calculated given irradiating X-rays from the X-ray tube 25 of the radiation therapy apparatus 10 to the 3-dimensional CT image and the 2-dimensional radiograph is calculated given irradiating X-rays from the X-ray tube 26 of the radiation therapy apparatus 10 to the 3-dimensional CT image. Such 2-dimensional radiographs are DRR images and generated by integrating the voxel values of each CT image data along the virtual X-ray path.

The initial parameter adjustment element 42 adjusts the initial projection geometry of the DRR image generated by the first virtual fluoroscopic projection parameters, i.e., the initial position of the fluoroscopic projection parameters with regards to rotation-and-translation of the CT image data based on the rough positional gap calculated by comparison between the DRR image and the radiograph. And the adjusted fluoroscopic projection parameters are the initial parameters when the evaluation standard (evaluation function) that evaluates a matching degree between both images is optimized so that the optimization element 43 can calculate more accurate gap between the DRR image and the radiographic image.

Figure 2:
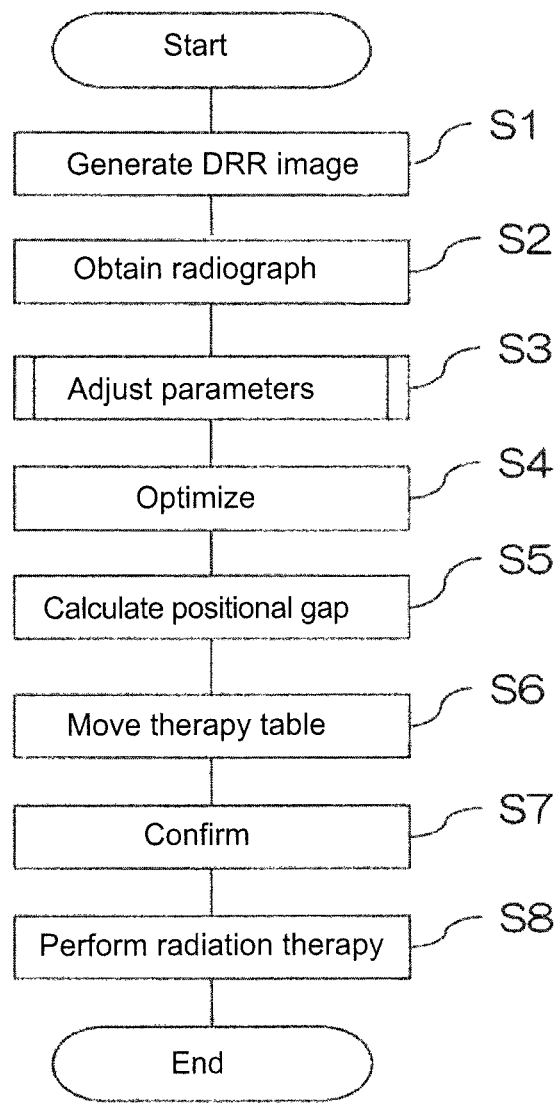
FIG. 2 is a flow-chart illustrating a procedure for a position determination relative to a patient 57.
Figure 3:
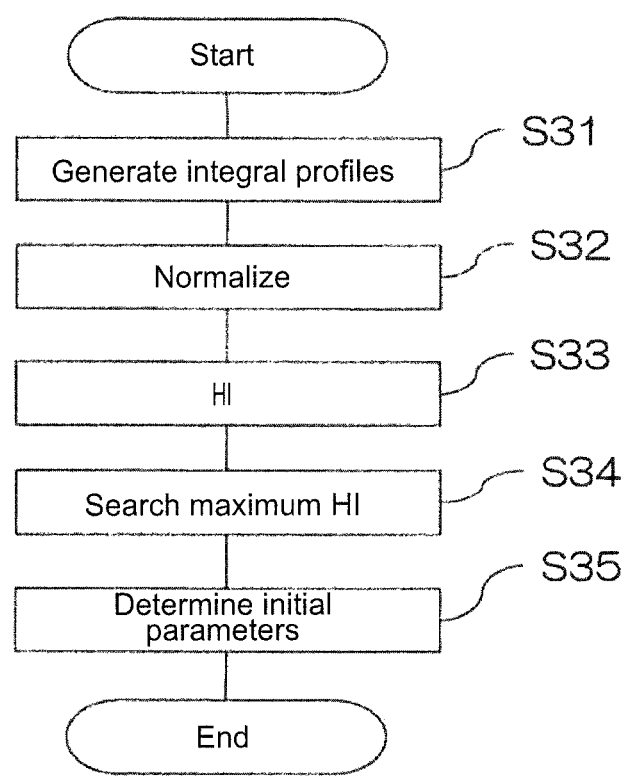
FIG. 3 is a flow-chart illustrating a procedure for an initial parameter adjustment prior to beginning an optimization operation.
Figure 4:
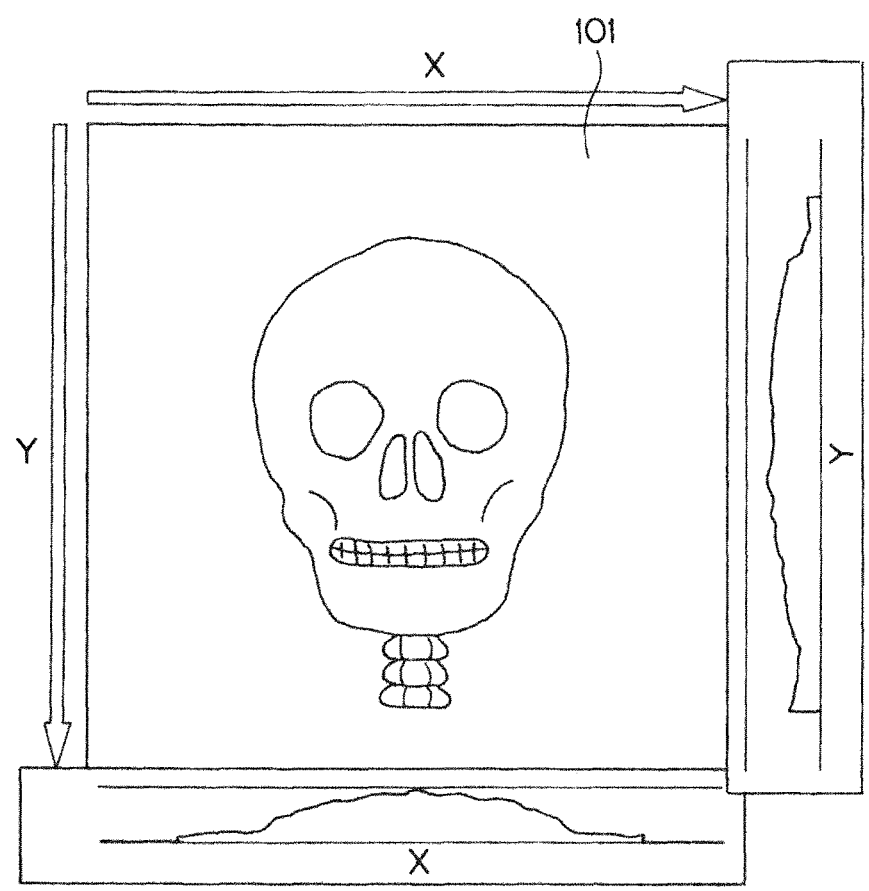
FIG. 4 is a schematic view illustrating a 1-dimensional integral profile of pixel values in the X-direction and the Y-direction of a radiograph 101.
Figure 5:
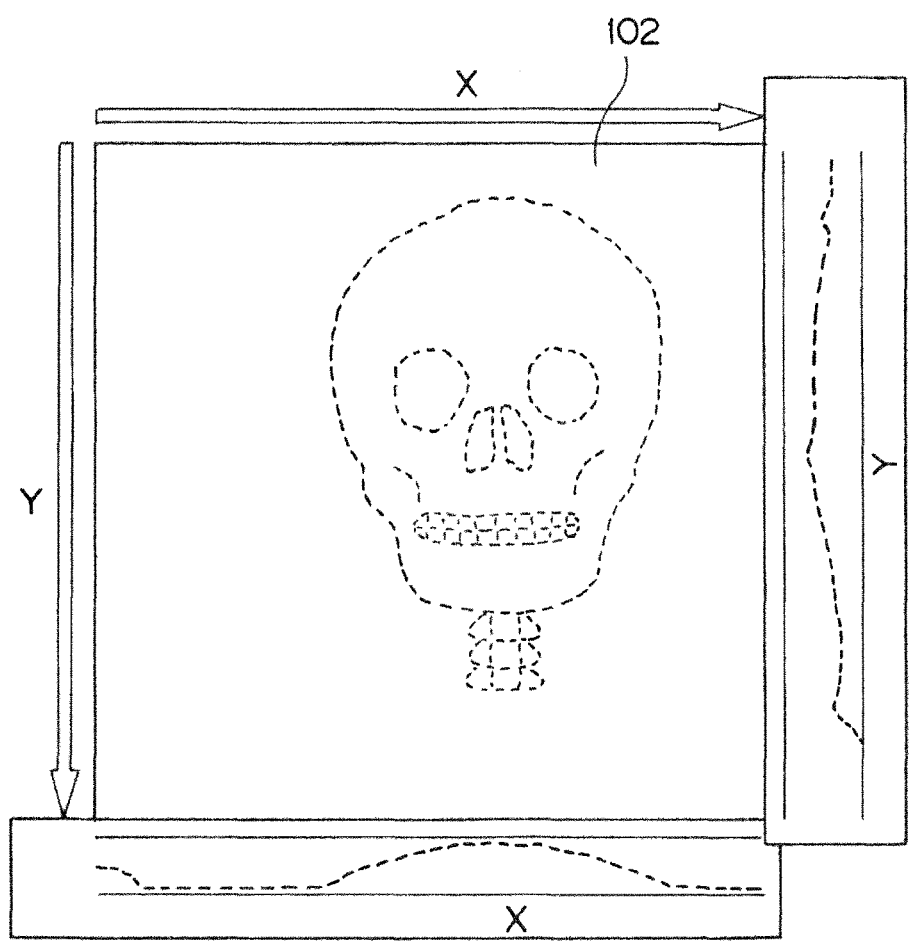
FIG. 5 is a schematic view illustrating a 1-dimensional integral profile of pixel values in the X-direction and the Y-direction of a DRR image 102.

Next, the inventor sets forth a positioning relative to the patient 57 by the radiation therapy apparatus 10 set forth above. FIG. 2 is a flow-chart illustrating a procedure for a positioning relative to a patient 57. FIG. 3 is a flow-chart illustrating a procedure for an initial parameter adjustment prior to beginning an optimization operation. FIG. 4 is a schematic view illustrating a 1-dimensional integral profile of radiograph 101 and FIG. 5 is a schematic view illustrating a 1-dimensional integral profile of the DRR image 102. In addition, referring to FIG. 4, the radiograph 101 is schematically illustrating a still image of the head of the patient 57 based on the detection value of the X-ray detector 23 and the head image of the patient 57 is indicated by the solid line. Referring to FIG. 5, the DRR image 102 is schematically illustrating a 2-dimensional image obtained by performing DRR along the X-ray path from the X-ray tube 25 referring to FIG. 1 to the X-ray detector 23 relative to the CT image data of the head of the patient 57, collected by the X-ray CT apparatus 14 in advance, and the head image of the patient 57 is indicated as the dashed line.

When the radiation therapy is performed, the radiotherapy table 27 is moved to position the patient 57 relative to the horizontal irradiation port 21 and the vertical irradiation port 22 so that the radiotherapy beam can be accurately irradiated to the affected region. When the positioning for the patient 57 is performed, the CT image data and other radiation treatment planning data are obtained from the patient DB 16 and the DRR image 102 is generated (Step S1). The radiation treatment planning data includes parameters such as irradiation direction of the radiation as the radiotherapy beam and so forth.

Next, the X-ray detector 23 and the X-ray detector 24 are in place in the location indicated by the phantom line referring to FIG. 1, and under such condition, X-rays are irradiated from the X-ray tube 25 and the X-ray tube 26 to the patient 57, so that the update image 101 of the patient 57 can be obtained (Step S2).

Then after, the initial parameters that is an initial position of the fluoroscopic projection parameters is adjusted using the DRR image 102 obtained at the Step S1 and the radiograph 101 obtained at the Step S2 prior to beginning the optimization operation to optimize the fluoroscopic projection parameters by the optimization element 43 (Step S3). In addition, the radiograph 101 referring to FIG. 4, and the DRR image 102 referring to FIG. 5 are displayed on the display element 47 if needed.

The adjustment of the preliminarily parameters is executed based on the procedure referring to FIG. 3. Firstly, a 1-dimensional integral profile by which the radiograph 101 and the DRR image 102 are integrated in the predetermined direction is generated (Step S31). Referring to FIG. 4 and FIG. 5, the integration direction is indicated by the arrow signs. Referring to FIGs., the 1-dimensional integral profile integrated in the width direction (X-direction) and the longitudinal direction (Y-direction) is calculated.

Figure 6:
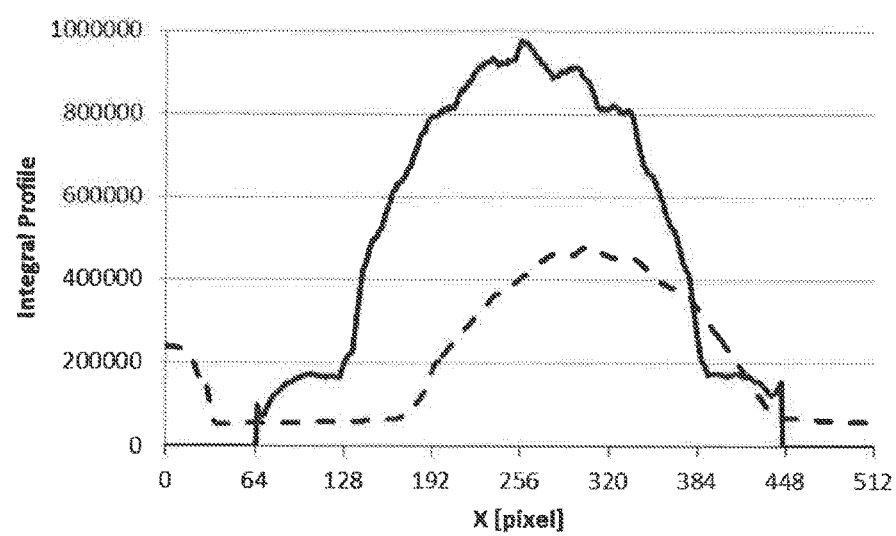
FIG. 6 is a schematic view illustrating the 1-dimensional integral profile in the X-direction of the radiograph 101 and the DRR image 102.
Figure 7:
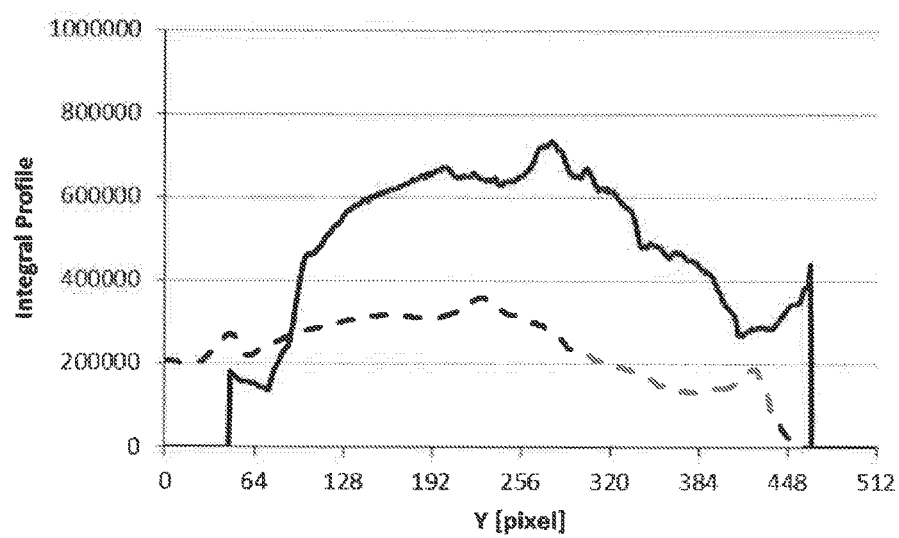
FIG. 7 is a schematic view illustrating the 1-dimensional integral profile in the Y-direction of the radiograph 101 and the DRR image 102.

FIG. 6 is a schematic view illustrating the 1-dimensional integral profile in the X-direction of the radiograph 101 and the DRR image 102 and FIG. 6 is a schematic view illustrating the 1-dimensional integral profile in the Y-direction of the radiograph 101 and the DRR image 102. The horizontal axis is pixel values and the vertical axis is integral values. Referring to FIG. 6, FIG. 7, the 1-dimensional integral profile of the radiograph 101 is indicated by the solid line and the 1-dimensional integral profile of the DRR image 102 is indicated by the dashed line.

Referring to FIG. 6, FIG. 7, the 1-dimensional integral profile of the radiograph 101 that images the patient 57 lying on the radiotherapy table 27 of the radiation therapy apparatus 10 and the 1-dimensional integral profile of the DRR image 102 generated from the CT image data are not matching at all. Such incident is due to the positional and angular gaps between the patient 57 lying on the radiotherapy table 27 of the radiation therapy apparatus 10 and the the patient 57 when the CT image data is collected, the difference of the quality of images and darkness between the radiograph 101 and the DRR image 102 thereof, and possible incorporated-or-not-incorporated image of the components of the radiotherapy table 27.

A normalization to make the scale unified relative to the 1-dimensional integral profile of the radiograph 101 and the DRR image 102, not matching each other, is performed. Such normalization is performed, given each 1-dimensional integral profile is a histogram, so that similarity of the respective 1-dimensional integral profiles can be evaluated by the histogram intersection HI set forth later. Specifically, the normalization is performed so that an area of the 1-dimensional integral profile H1[i] of the radiograph 101 can match an area of the 1-dimensional integral profile H2[i] of the DRR image 102 based on the following mathematical formula 1 (Step S32).

Mathematical Formula 1

$$\overline{H1}[i] = H1[i] \times \frac{\sum_i H2[i]}{\sum_i H1[i]} \quad (1)$$

Figure 8:
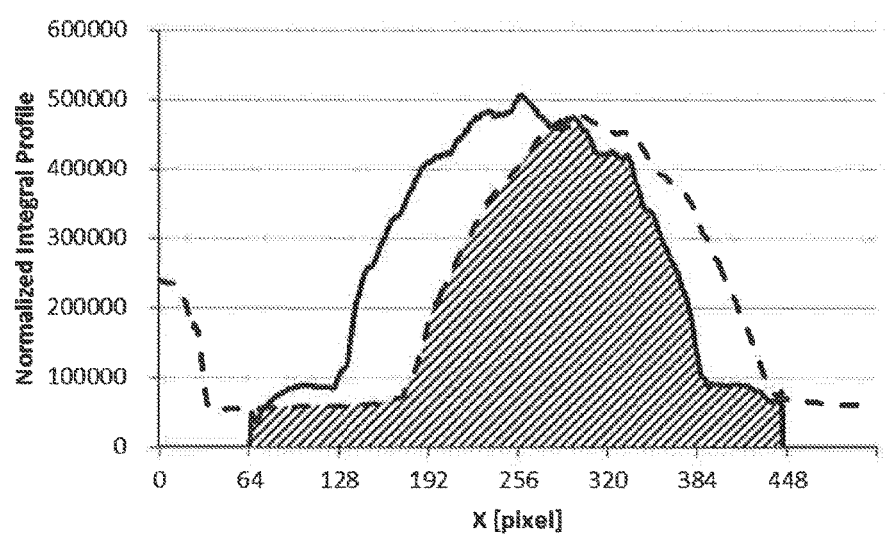
FIG. 8 is a graph illustrating a normalized integral profile that normalizes the graph in FIG. 6, and a histogram intersection HI.
Figure 9:
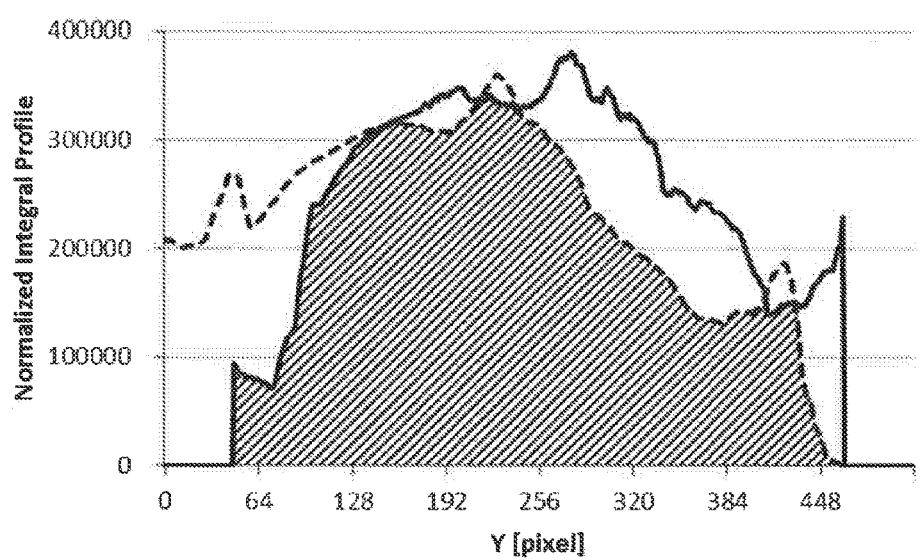
FIG. 9 is a graph illustrating a normalized integral profile that normalizes the graph in FIG. 7 and a histogram intersection HI.

FIG. 8 is the graph illustrating the normalized integral profile that normalizes the graph in FIG. 6 and the histogram intersection HI. FIG. 9 is the graph illustrating the normalized integral profile that normalizes the graph in FIG. 7 and the histogram intersection HI. Referring to FIG. 8, FIG. 9, the normalized integral profile of the radiograph 101 is indicated by the solid line and the normalized integral profile of the DRR image 102 is indicated by the dashed line.

In addition, such normalization can simultaneously do also adjust the concentration difference between the radiograph 101 and the DRR image 102. Specifically, an effect of e.g., image quality difference between images on the 1-dimensional integral profile is minor, so that it is feasible to make concentration of the patient image uniformed at a practical accuracy level. Here, the DRR CT image 102 simulates the radiograph 101 using the CT image data, so that the concentration can be uniformed with only adjusting the gain of the X-ray exposure but without adjusting the concentration distribution width of CT values. In addition, when the width of concentration distribution of CT values needs to be adjusted, conventional WL (window level)/WW (window width) processing can be used together to uniform the concentrations between images.

Next, the position at which the 1-dimensional integral profile (hereafter normalized integral profile) is most similar following normalization of the radiograph 101 and the DRR image 102 in the same direction is searched for. Such search is to obtain the similarity of both normalized integral profiles of the radiograph 101 and the DRR image 102 using the histogram intersection HI from the following mathematical formula (2) (Step S33).

Mathematical Formula 2

$$HI = \frac{\sum_i \min(\overline{H1}[i], H2[i])}{\sum_i H2[i]} \quad (2)$$

Referring to FIG. 8, as set forth above, in accordance with normalization, the histogram area of the radiograph 101 surrounded by the solid line coincides with the histogram area of the DRR image 102 surrounded by the dashed line. In addition, referring to FIG. 9, the histogram area of the radiograph 101 surrounded by the solid line coincides with the histogram area of the DRR image 102 surrounded by the dashed line. Referring to FIG. 8 and FIG. 9, as indicated by hatching, the histogram intersection HI is the percentage of the superimposed histogram of the radiograph 101 and the DRR Image 102 relative to the area of histogram. Accordingly, the value of the histogram intersection HI is not less than 0 and not more than 1, and the closer to 1 the value is, in the higher degree the histograms match.

The position at which the degree of matching is highest is the position where both normalized integral profiles of the radiograph and the DRR image are most similar. And it is supposed that both images are superimposed most at such position. Accordingly, the position where the matching degree of histograms is highest, i.e., the position where the histogram intersection HI becomes maximum is searched (Step 34). The search in the Step 34 is performed by calculating the histogram intersection HI while moving the position of normalized integral profile of the other image along the horizontal axis, referring to FIG. 8 and FIG. 9, relative to the position of the normalized integral profile of the one image.

Figure 10:
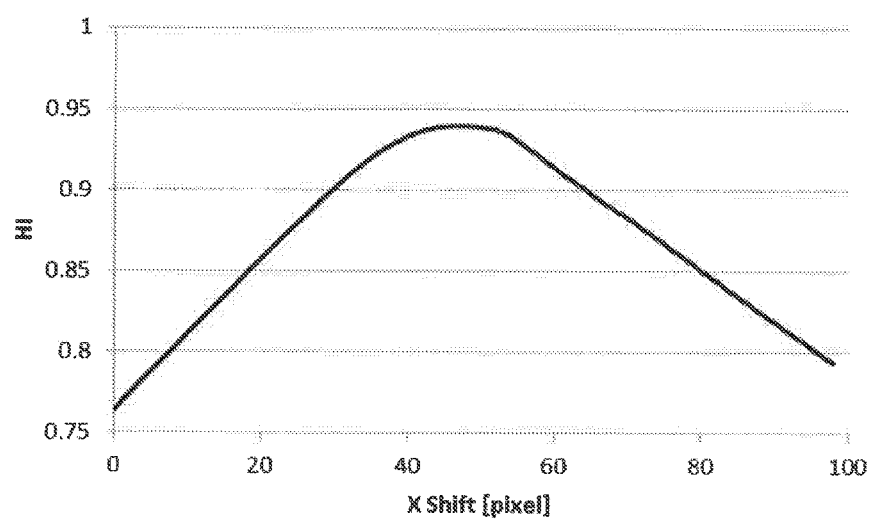
FIG. 10 is a graph illustrating a variation of the histogram intersection HI when the normalized integral profile in FIG. 8 is shifted
Figure 11:
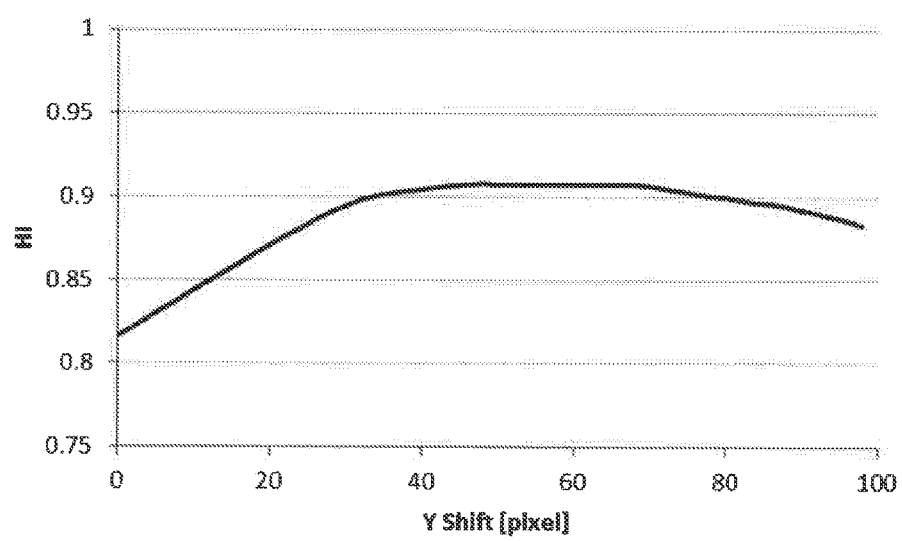
FIG. 11 is a graph illustrating a variation of the histogram intersection HI when the normalized integral profile in FIG. 9 is shifted.

FIG. 10 is a graph illustrating a variation of the histogram intersection HI when the normalized integral profile in FIG. 8 is moved, and FIG. 11 is a graph illustrating a variation of the histogram intersection HI when the normalized integral profile in FIG. 9 is moved, the horizontal axis of the graph is the numbers of moving pixels and the vertical axis is the histogram intersection HI.

The histogram intersection HI becomes as indicated in FIG. 10, FIG. 11 when gaps when the position of normalized integral profile of the other image (DRR image 102) is gapped to the horizontal axis direction of the graphs referring to FIG. 8 and FIG. 9, relative to the position of the normalized integral profile of the one image (radiograph 101). Referring to FIG. 10, the peak of the histogram intersection HI is clear, so that the search of the normalized integral profile position at which the histogram intersection HI becomes maximum can be facilitated. The calculation cost of the histogram intersection HI using the normalized integral profile can be significantly smaller than the calculation cost using the image per se. Therefore, the search of the maximum value of the histogram intersection HI can be calculated exhaustively or can be performed using a 1-dimensional optimization method such as Brent method.

On the other hand, as the variation of the histogram intersection HI referring to FIG. 11, the peak of the histogram intersection HI becomes flat, so that the search of the normalized integral profile position at which the histogram intersection HI becomes maximum may be difficult. For example, when there is difference relative to incorporations of e.g., the radiotherapy table 27 between images to be compared, the histogram intersection HI becomes such variation as indicated in FIG. 11. In such way, when the maximums of the histogram intersection HI are plural, the center of the flat part can be set as the maximum value.

When the search of the maximum of the histogram intersection HI is completed, the position at which the histogram intersection HI is maximum is set as an initial position of the fluoroscopic projection parameters (Step S35).

Figure 12:
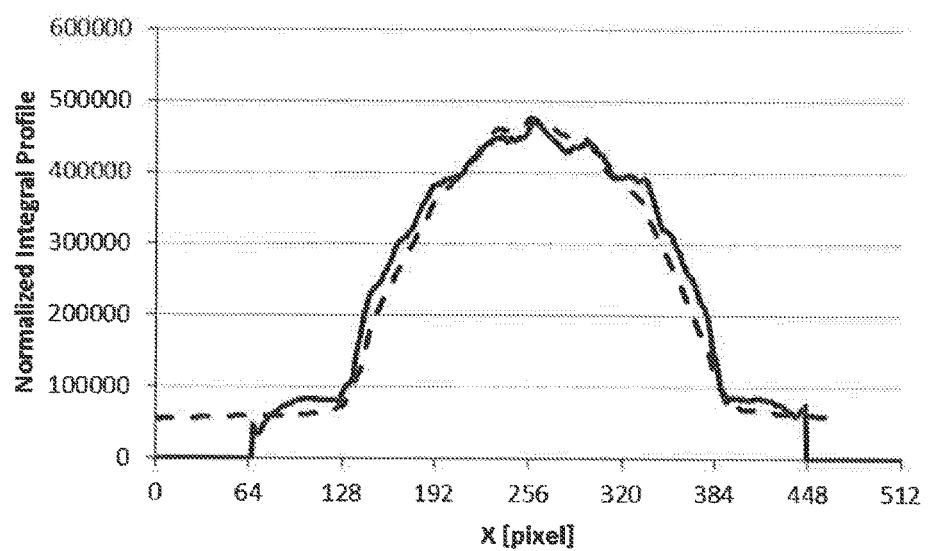
FIG. 12 is a graph illustrating the normalized integral profile in the X-direction after an initial parameter adjustment.
Figure 13:
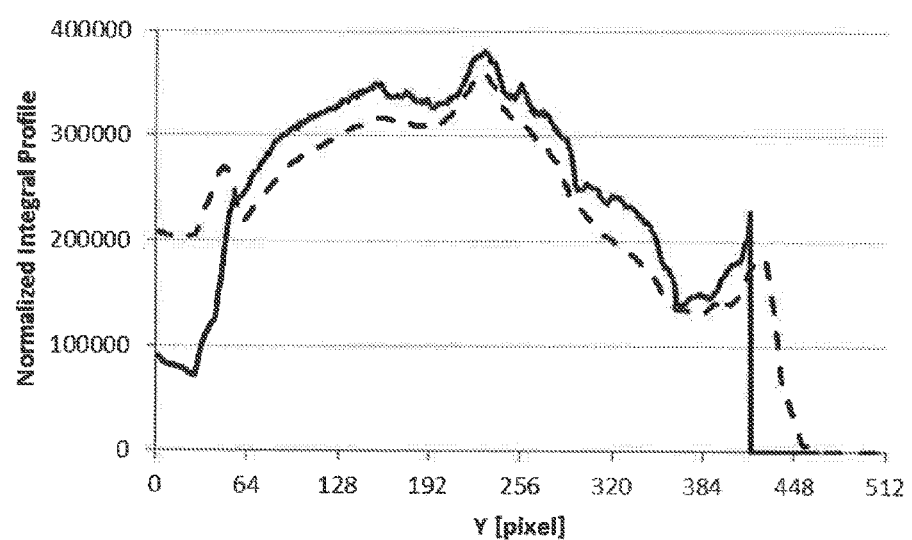
FIG. 13 is a graph illustrating the normalized integral profile in the Y-direction after an initial parameter adjustment.
Figure 14:
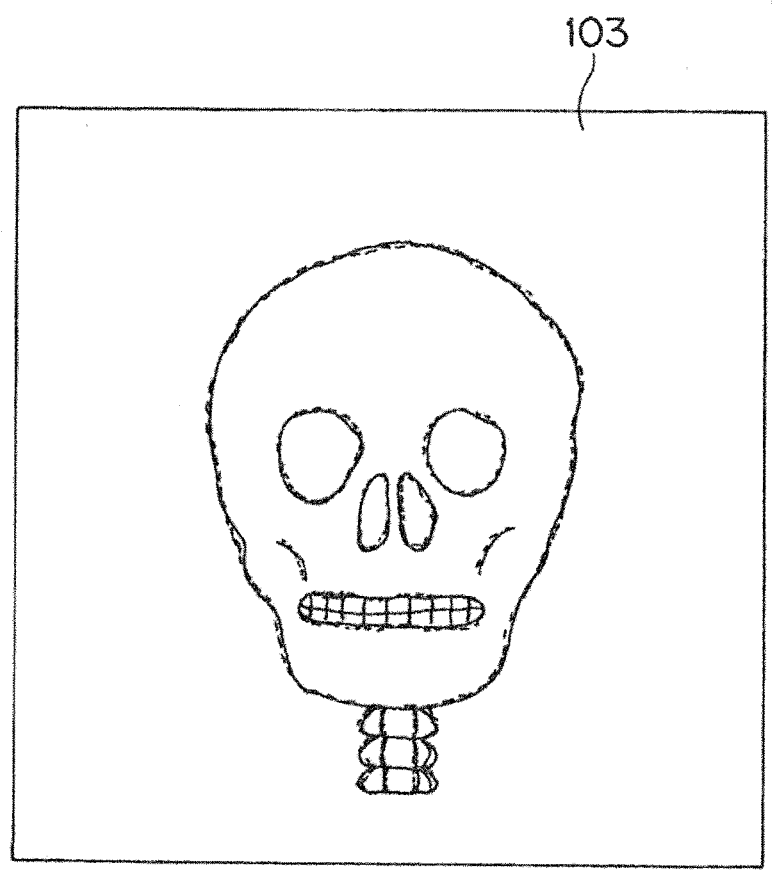
FIG. 14 is a schematic view illustrating a superimposed image 103 of the radiograph 101 and the DRR image 102 after an initial parameter adjustment.

FIG. 12 is a graph illustrating the normalized integral profile in the X-direction of the radiograph 101 and the DRR image 102 at which the histogram intersection HI becomes maximum. FIG. 13 is a graph illustrating the normalized integral profile in the Y-direction of the radiograph 101 and the DRR image 102 at which the histogram intersection HI becomes maximum. FIG. 14 is a schematic view illustrating a superimposed image 103 of the radiograph 101 and the DRR image 102, after the initial parameter is adjusted in the position at which the histogram intersection HI becomes maximum referring to FIG. 12, FIG. 13. Referring to FIG. 14, the head image of the patient 57 originated from the radiograph 101 is indicated as the solid line and the head image of the patient 57 originated from the DRR image 102 is indicated as the dashed line FIG. 12 is a schematic view illustrating the 1-dimensional integral profile in the X-direction of the radiograph 101 and the DRR image 102. Referring to FIG. 13, the normalized integral profile in the Y-direction is similar each other. In addition, the shape per se of the histogram is different each other based on the different position of the patient 57 and the different angle and so forth between the normalized integral profile of the radiograph 101 and the normalized integral profile of the DRR image 102, so that both never match completely. Specifically, the position at which both normalized integral profiles are most similar do not exactly match to the position at which the radiograph 101 and the DRR image 102 are superimposed. However, the purpose of the initial parameter adjustment (Step S3) is to bring the fluoroscopic projection geometry closer to the geometry of the actual X-ray radiography system to prevent that the solution on the optimization operation goes into the local solution relative to the optimization (Step 4) at the later step. Specifically, from the initial parameter adjustment standpoint prior to beginning the optimization operation, setting the position as the initial position, prior to an optimization operation, at which the normalized integral profiles of the radiograph 101 and the DRR image 102 that are obtained by the procedures (Steps S31 to S34), set forth above are most similar, is deemed fully practical as the accuracy degree as to the rough adjustment of the position of the patient 57.

In addition, examples referring to FIG. 4 to FIG. 14, illustrates the cases in which the radiograph 101 and the DRR image 102 are 2-dimensional images of the X-Y plane in which the center of image is an X-ray irradiation axis from the X-ray tube 25 to the X-ray detector 23, but also the initial position prior to the optimization operation relative to the 2-dimensional images of the Y-Z plane in which the center of image is an X-ray irradiation axis from the X-ray tube 26 to the X-ray detector 24 can be automatically determined using the same procedure.

When the adjustment of the initial parameter is completed, referring to FIG. 14, the superimposed image 103 of the radiograph 101 and the DRR image 102 is displayed on the display 47 as the image after rough position adjustment. Further, an optimization of the fluoroscopic projection parameters is performed, and the positional gap between the update position of the patient 57 and the position of the patient 57 on the CT image data is calculated (Step SS). The positional gap is converted to the shift distance and a radiotherapy table moving control element 32 shifts the radiotherapy table 27 (Step S6).

After the radiotherapy table 27 is shifted, the radiograph is re-obtained and the operator visually confirms the image displayed on the display 47 and the gap between the radiograph 101 and the DRR image 102 is automatically confirmed whether it is in the acceptable range as an error range of the irradiation position of the radiotherapy beam (Step S7). Since it is confirmed that the positioning of the patient 57 is adequately performed, the X-ray detector 23 and the X-ray detector 24 are moved to the position indicated by the solid line referring to FIG. 1 and the radiation therapy is performed to irradiate the radiotherapy beam to the affected region of the patient 57 (Step S8).

Conventionally, a DRR image is generated at the first step of the optimization operation, but according to the aspect of the present Embodiment set forth above, the DRR image 102 is generated prior to adjustment of the initial parameter. In addition, such DRR image 102 can be applied to the optimization operation.

According to the aspect of the Embodiment set forth above, a positioning apparatus 40 is applied to a radiation therapy apparatus 10, but also, e.g., it is feasible that the positioning apparatus of the present invention is applied to an X-ray fluoroscopic table being used for performing cardiac catheterization radiotherapy and a 3-dimensional image of the heart obtained by an X-ray CT apparatus in advance and an update position of the patient can be positioned.

Field of the Invention

The present invention relates to a positioning apparatus and a method of the same in the radiation therapy area, in which X-ray, electron beam, and corpuscular radiation are irradiated to the affected cancer region of the patient, and has an industrial applicability.

REFERENCE OF SIGN

10 Radiation therapy apparatus
14 X-ray CT apparatus
15 Radiation treatment planning device
16 Patient DB
17 Network
21 Horizontal irradiation port
22 Vertical irradiation port
23 X-ray detector
24 X-ray detector
25 X-ray tube
26 X-ray tube
27 Radiotherapy table
Radiotherapy control device
31 Radiotherapy beam irradiation control element
32 Radiotherapy table moving control element
33 X-ray fluoroscopic imaging control element
40 Positioning apparatus
41 DRR image generation element
42 Initial parameter adjustment element
43 Optimization element
47 Display element
57 Patient
101 Radiograph
102 DRR image
103 Superimposed image As used herein, a computer-type system" comprises an input device for receiving data, an output device for outputting data in tangible form (e.g. printing or displaying on a computer screen or transmitting data, or performing a calculation, etc.), a permanent-or-temporary memory for storing data as well as computer code, and a microprocessor for executing computer code wherein said computer code resident in said permanent memory will physically cause said microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, elements, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A positioning apparatus, comprising:
   a DRR image generation element that obtains a DRR image by performing virtually a fluoroscopic projection on X-ray CT image data of an X-ray CT image collected in advance and reconstructing a geometric arrangement of an X-ray radiography system; and
   an optimization element performs an optimization operation that calculates a positional gap between a position of a patient when the X-ray CT image data are collected and an actual position of the patient at which the X-ray radiography system performs a radiography on the patient and creates an actual image, wherein fluoroscopic projection parameters relative to rotation-and-translation of the X-ray CT image are optimized to maximize an evaluation function that evaluates a matching degree between said DRR image obtained by the DRR image generation element and said actual image obtained by the X-ray radiography system;
   an initial parameter adjustment element that, prior to beginning the optimization operation that optimizes said fluoroscopic projection parameters using said optimization element, changes an initial position of said fluoroscopic projection parameters based on a rough positional gap; wherein the rough positional gap of the patient is calculated from the positional gap between said DRR image and said actual image.

2. The positioning apparatus, according to claim 1, wherein:
   said initial parameter adjustment element respectively calculates a 1-dimensional integral profile that integrates said DRR image in a predetermined direction and a 1-dimensional integral profile that integrates said actual image in the predetermined direction, and calculates said rough positional gap by initially executing a comparison between the 1-dimensional integral profiles in the same direction relative to said DRR image and said actual image.

3. The positioning apparatus, according to claim 2, wherein:
   said initial parameter adjustment element calculates a similarity degree valuation between histograms, as said 1-dimensional integral profile that integrates said DRR image in the predetermined direction and said 1-dimensional integral profile that integrates said actual image in the predetermined direction are histograms, relative to a comparison between said 1-dimensional integral profile that integrates said DRR image in the predetermined direction and said 1-dimensional integral profile that integrates said actual image in the predetermined direction, and further sets as the initial position of said fluoroscopic projection parameters, wherein the similarity degree between such histograms becomes maximum.

4. A positioning method, comprising the steps of:
   generating a DRR
   by reconstructing a geometric arrangement of an X-ray radiography system on a computer and performing virtually a fluoroscopic projection on X-ray CT image data collected in advance; and
   optimizing a calculation that calculates a gap between a position of a patient when the X-ray CT image data are collected and an actual position of the patient at which the X-ray radiography system performs a radiography on the patient;
   optimizing fluoroscopic projection parameters relative to a rotation-and-translation of said X-ray CT image data so that evaluation functions that evaluate a matching degree between said DRR image obtained by said step of generating said DRR image and an actual image obtained by the X-ray radiography system can be maximized;

adjusting an initial parameter that changes an initial position of said fluoroscopic projection parameters based on a rough positional gap; and calculating the rough positional gap from a gap between said DRR image and said actual image prior to beginning said step of optimizing fluoroscopic projection parameters.

5. The positioning method, according to claim 4, wherein:

said step of adjusting said initial parameter further respectively calculates a first 1-dimensional integral profile that integrates said DRR image in a predetermined direction and a second 1-dimensional integral profile that integrates the actual image in a predetermined direction, and calculates said rough positional gap by executing the comparison between the first and second 1-dimensional integral profiles of in the same direction relative to said DRR image and said actual image.

6. The positioning method, according to claim 5, wherein:

said step of adjusting said initial parameter calculates a similarity degree between histograms, as said first 1-dimensional integral profile that integrates said DRR image in the predetermined direction and said second 1-dimensional integral profile that integrates said actual image in the predetermined direction are histograms, relative to comparison between said first 1-dimensional integral profile that integrates said DRR image in the predetermined direction and said second 1-dimensional integral profile that integrates said actual image in the predetermined direction, and sets as ]an initial position of said fluoroscopic projection parameters, at which the similarity degree between such histograms becomes maximum.

* * * * *